(12) United States Patent
Hedström et al.

(10) Patent No.: US 6,479,078 B1
(45) Date of Patent: Nov. 12, 2002

(54) SUBSTANTIALLY CRYSTALLINE FORM OF MELAGATRAN

(75) Inventors: Lena Hedström, Täby (SE); Anita Lundblad, Västra Frölunda (SE); Sofia Någård, Göteborg (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/623,165

(22) PCT Filed: Jun. 30, 2000

(86) PCT No.: PCT/SE00/01398

§ 371 (c)(1),
(2), (4) Date: Aug. 28, 2000

(87) PCT Pub. No.: WO01/02426

PCT Pub. Date: Jan. 11, 2001

(30) Foreign Application Priority Data

Jul. 2, 1999 (SE) .................................... 9902550

(51) Int. Cl.[7] .......................... A61K 9/14; A61K 31/395
(52) U.S. Cl. .................................. 424/489; 514/210.01
(58) Field of Search ...................... 424/489; 514/210.01

(56) References Cited

U.S. PATENT DOCUMENTS 6,225,287 B1    5/2001   Edvardsson et al.

FOREIGN PATENT DOCUMENTS

| WO | 94/29336 | 12/1994 |
| WO | 96/16671 | 6/1996 |
| WO | WO 98/16252 | * 4/1998 |
| WO | 00/14110 | 11/2000 |
| WO | 00/67727 | 11/2000 |

OTHER PUBLICATIONS

Remington's Pharmaceutical Sciences, 18 edition, p 1615.*

* cited by examiner

Primary Examiner—Thurman K. Page
Assistant Examiner—A. Pulliam
(74) Attorney, Agent, or Firm—Nixon & Vanderhye

(57) ABSTRACT

There is provided melagatran in a form which is substantially crystalline. It has been found that crystalline forms of melagatran have a high chemical and solid state stability when compared to amorphous forms of the compound.

24 Claims, 4 Drawing Sheets

1/d - Scale

SUBSTANTIALLY CRYSTALLINE FORM OF MELAGATRAN

FIELD OF THE INVENTION

This invention relates to new solid state forms of a drug, to pharmaceutical compositions containing them, and to processes for obtaining them.

BACKGROUND OF THE INVENTION

In the formulation of drug compositions, it is important for the drug substance to be in a form in which it can be conveniently handled and processed. This is of importance, not only from the point of view of obtaining a commercially viable manufacturing process, but also from the point of view of subsequent manufacture of pharmaceutical formulations comprising the active compound.

Further, in the manufacture of drug compositions, it is important that a reliable, reproducible and constant plasma concentration profile of drug is provided following administration to a patient. This is of particular importance in the manufacture of compositions comprising antithrombotic agents.

Chemical stability, solid state stability, and "shelf life" of the active ingredients are also very important factors. The drug substance, and compositions containing it, should be capable of being effectively stored over appreciable periods of time, without exhibiting a significant change in the active component's physico-chemical characteristics (e.g. its chemical composition, density, hygroscopicity and solubility).

Moreover, it is also important to be able to provide drug in a form which is as chemically pure as possible.

Amorphous materials may present significant problems in this regard. For example, such materials are typically difficult to handle and to formulate, provide for unreliable solubility, and are often found to be unstable and chemically impure.

The skilled person will appreciate that, if a drug can be readily obtained in a stable crystalline form, the above problems may be solved.

Thus, in the manufacture of commercially viable, and pharmaceutically acceptable, drug compositions, it is important, wherever possible, to provide drug in a substantially crystalline, and stable, form.

It is to be noted, however, that this goal is not always achievable. Indeed, typically, it is not possible to predict, from molecular structure alone, what the crystallisation behaviour of a compound will be. This can usually only be determined empirically.

PRIOR ART

International patent application WO 94/29336 discloses a number of compounds, which are useful as inhibitors of serine proteases, such as thrombin, including the compound,

wherein Cgl represents cyclohexylglycine, Aze represents azetidine-2-carboxylate and Pab-H represents 4-aminomethylamidinobenzene. The compound is also known as melagatran (glycine, N-[(1R)-2-[(2S)-2-[[[[4-(aminoiminomethyl)phenyl] methyl] amino] carbonyl]-1-azetidinyl]-1-cyclohexyl-2-oxoethyl]-).

A process for the synthesis of this compound is described in Example 1 of WO 94/29336, where it is obtained as crude material, by evaporation of reaction solvent following a final deprotection step. The compound is thus isolated in an amorphous form.

Whether it is possible to provide melagatran in a crystalline form is not disclosed in WO 94/29336. Furthermore, no information is provided in relation to how this compound may be obtained in such a form and, more particularly, how it may be obtained in a chemically, and/or solid state, stable form.

DISCLOSURE OF THE INVENTION

We have found that melagatran may be readily obtained in one or more forms that are both substantially crystalline and stable in nature.

Thus, according to a first aspect of the invention there is provided melagatran in a substantially crystalline form (hereinafter referred to as "the compounds of the invention").

Although we have found that it is possible to produce melagatran in forms which are greater than 80% crystalline, by "substantially crystalline" we include greater than 20%, preferably greater than 30%, and more preferably greater than 40% crystalline. The degree (%) of crystallinity may be determined by the skilled person using X-ray powder diffraction (XRPD). Other techniques, such as solid state NMR, FT-IR, Raman spectroscopy, differential scanning calorimetry (DSC) and microcalorimetry, may also be used.

The compounds of the invention may be in the form of a solvate, a hydrate or a mixed solvate/hydrate. Solvates may be of one or more organic solvents, such as lower alkyl (e.g. $C_{1-4}$ alkyl) alcohols (e.g. methanol, ethanol or iso-propanol) or mixtures thereof.

We have found that the compounds of the invention have a surprisingly improved stability when compared with melagatran prepared as described in WO 94/29336.

According to a further aspect of the invention, there is thus provided a stable form of melagatran.

The term "stability" as defined herein includes chemical stability and solid state stability.

By "chemical stability", we include that the compound can be stored in an isolated solid form, or in the form of a solid formulation in which it may be provided in admixture with pharmaceutically acceptable carriers, diluents or adjuvants, under normal storage conditions, with an insignificant degree of chemical degradation or decomposition.

By "solid state stability", we include that the compound can be stored in an isolated solid form, or in the form of a solid formulation in which it may be provided in admixture with pharmaceutically acceptable carriers, diluents or adjuvants, under normal storage conditions with an insignificant degree of solid state transformation (e.g. crystallisation, recrystallisation, solid state phase transition, hydration, dehydration, solvatisation or desolvatisation).

Examples of "normal storage conditions" include temperatures of between minus 80 and plus 50° C. (preferably between 0 and 40° C. and more preferably ambient temperature, such as between 15 and 30° C.), pressures of between 0.1 and 2 bars (preferably atmospheric pressure), and/or exposure to 460 lux of UV/visible light, for prolonged periods (i.e. greater than or equal to six months). Under such conditions, compounds of the invention may be found to be less than 15%, more preferably less than 10%, and especially less than 5%, chemically degraded/decomposed, or solid-state transformed, as appropriate. The skilled person will appreciate that the above-mentioned upper and lower limits for temperature and pressure represent extremes of normal storage conditions, and that certain combinations of these extremes will not be experienced during normal storage (e.g. a temperature of 50° C. and a pressure of 0.1 bar).

The term "normal storage conditions" may also include relative humidities of between 5 and 95% (preferably 10 to 75%). However, in the case of certain crystalline forms according to the invention, changes in conformation or crystal structure by hydration and/or dehydration may occur as a result of prolonged exposure to certain extremes of relative humidities, at normal temperatures/pressures. For example, we have found that crystalline forms of melagatran that are in the form of a hydrate (e.g. a monohydrate) may be stored at 10% relative humidity or above at ambient temperature/atmospheric pressure with an insignificant degree of dehydration. However, we have also found that crystalline forms of melagatran that are in the form of an anhydrate should be stored at less than 40% (preferably less than 30%, more preferably less than 20%) relative humidity at ambient temperature/atmospheric pressure, to maintain an insignificant degree of hydration.

Thus, although compounds of the invention possess a greater solid state stability than forms of melagatran described in the prior art, some compounds of the invention are more solid state stable than others. In this respect, it will be appreciated by the skilled person that storage conditions may be tailored to suit the crystalline form that is being stored.

The compounds of the invention may be obtained advantageously by crystallising melagatran.

According to a further aspect of the invention, there is provided a process for the production of a compound of the invention which comprises crystallising melagatran.

Although metagatran may be crystallised with or without the presence of a solvent system (e.g. crystallisation may be from a melt, under supercritical conditions, or achieved by sublimation), we prefer that the crystallisation is from an appropriate solvent system.

We have found that it is possible to obtain crystalline melagatran via crystallisation advantageously following dissolution and/or suspension of the compound, or, more advantageously, from reaction solutions within which the compound has been formed.

The solvent system may include one or more organic solvents, such as alkyl acetates (e.g. linear or branched $C_{1-6}$ alkyl acetates, such as ethyl acetate, iso-propyl acetate and butyl acetate), lower (e.g. linear or branched $C_{1-6}$, preferably $C_{2-4}$) alkyl alcohols (e.g. ethanol, iso-propanol), aliphatic and aromatic hydrocarbons (e.g. iso-octane, n-heptane and toluene), dialkyl ketones (e.g. methyl ethyl ketone and methyl iso-butyl ketone), dialkyl ethers (e.g. di-iso-propyl ether) and acetonitrile. Mixtures of any of the abovementioned solvents may be used. Organic solvents may also be admixed with water or aqueous solutions.

Different crystalline forms may have different solubilities in different organic solvents at any given temperature. In this respect, above-mentioned solvents may be employed as "antisolvents" (i.e. a solvent in which compounds of the invention are poorly soluble), and may thus aid the crystallisation process. Lower alkyl alcohols are preferred solvents. When lower alkyl alcohols are employed as solvent, other solvents identified above may be employed as antisolvents (especially acetonitrile and ethyl acetate).

When the crystallisation takes place from a reaction solution in which melagatran has been formed, suitable solvents include lower alkyl alcohols (e.g. methanol, ethanol or iso-propanol) which may be in admixture with water.

Crystallisation of compounds of the invention from an appropriate solvent system may be achieved by attaining supersaturation in a solvent system which comprises melagatran (e.g. by cooling, by solvent evaporation, and/or via the addition of a suitable antisolvent). Crystallisation may also be effected by decreasing the solubility of the substance by the addition of a salt (such as NaCl).

The skilled person will appreciate that the concentration in solution of the compound that is to be crystallised, and the solvent system that is used, may influence crystallisation temperatures and crystallisation times.

The compounds of the invention may be in the form of a solvate, a hydrate or a mixed solvate/hydrate.

Compounds of the invention may also be in the form of an anhydrate. (The term "anhydrate", when used in this context, also includes compounds that are "ansolvates".) To ensure that anhydrate is produced, the solvent from which the crystallisation occurs should be dried, either before or during the crystallisation process, in order to reduce the water content below a critical level, which should preferably not be exceeded during the crystallisation. Solvent may be dried during the crystallisation process, for example by decreasing the water content of a mixture of the compound to be crystallised and an appropriate organic solvent/aqueous solvent system (e.g. by increasing the amount of organic solvent that is present and/or removal of water by formation of an azeotrope, with successive distillations). The "critical level" of water depends upon factors such as temperature, concentration in solution of the compound to be crystallised, impurity profile, and the solvent system which is employed, but may be determined non-inventively.

Thus, anhydrate may be produced by crystallisation from a solvent system, including one or more organic solvents (such as lower (e.g. $C_{2-6}$) alkyl alcohols (e.g. ethanol, iso-propanol), acetonitrile and/or ethyl acetate) and/or water, which solvent system is, or is rendered during the crystallisation process, substantially free of water. By "substantially free of water", we include that the water content in the solvent system is below that which will result in the formation of, at most, 20% monohydrate, for any particular solvent system and set of crystallisation conditions.

To ensure that monohydrate is produced, water must be present in the solvent from which the crystallisation occurs. The water content should preferably be above a critical level during the crystallisation (which "critical level" will depend upon the factors mentioned above in respect of production of anhydrate). Thus, crystalline monohydrate may be prepared by crystallising melagatran from a solvent system comprising water, and/or one or more organic solvents, including ethyl acetate, ethanol, iso-propanol, methyl iso-butyl ketone, methyl ethyl ketone, acetonitrile and mixtures thereof.

To ensure that a solvate is produced, an appropriate organic solvent, capable of forming a solvate, must be present as part of the solvent system from which the crystallisation occurs. Solvates that are in the form of "mixed" solvate/hydrate may also be prepared. For example, we have found that mixed lower alkyl (e.g. $C_{1-4}$ alkyl) alcohol (e.g. methanol, ethanol and/or iso-propanol) solvate/hydrates may be prepared by crystallising a compound of the invention from a mixture of lower alkyl alcohols (e.g. methanol, ethanol and/or iso-propanol), water and an antisolvent (e. g. acetonitrile), for example as described hereinafter.

According to a further aspect of the invention, there is provided a compound of the invention that is in the form of a solvate, a compound of the invention that is in the form of a monohydrate, a compound of the invention that is in the form of a mixed lower (e.g. $C_{1-4}$) alkyl alcoholate/hydrate (e.g. an iso-propanol solvate/hydrate), and a compound of the invention that is in the form of an anhydrate.

As may be appreciated by the skilled person, the crystalline form that is obtained depends upon both the kinetics and the thermodynamics of the crystallisation process. Under certain thermodynamic conditions (solvent system, temperature, pressure and concentration of the compound of the invention), one crystalline form may be more stable than another (or indeed any other). However, other crystalline forms that may have, in comparison, a relatively low thermodynamic stability, may be kinetically-favoured. Thus, in addition, kinetic factors, such as time, impurity profile, agitation, the presence of seeds, etc. may also influence which forms appear. Thus, the procedures discussed herein may be adapted by the skilled person as appropriate in order to obtain different crystalline forms of melagatran.

In order to ensure that crystalline forms as described herein are prepared in the absence of other crystalline forms described herein, crystallisations are preferably carried out by seeding with nuclei and/or seed crystals of the desired crystalline form in the complete absence of nuclei and/or seed crystals of other crystalline forms described herein.

Compounds of the invention that are anhydrates contain no more than 3%, preferably 1% and more preferably 0.5% (w/w) water, whether such water is bound (crystal water or otherwise) or not. Solvates, hydrates and mixed hydrates/solvates contain no less than 0.5 mol of solvent and/or water (as appropriate) per mol of melagatran.

Preferred compounds of the invention are those that are in the form of a hydrate, such as a monohydrate. According to a further aspect of the invention, there is provided a compound of the invention that contains at least 0.5, preferably 0.85 and more preferably 0.90 mol water per mol of melagatran, whether such water is bound (crystal water or otherwise) or not.

We have also found that compounds of the invention in one crystalline form can be converted into other crystalline forms. For example, crystalline monohydrate may also be formed by elutriation of other crystalline forms (e.g. anhydrates and/or other solvates) in water or a mixture of a sufficient amount of water and one or several organic solvents (such as ethanol, iso-propanol, ethyl acetate, acetonitrile or methyl iso-butyl ketone). The slurry that is formed may preferably be seeded with crystals of the crystalline monohydrate in order to ensure that an appropriate transformation takes place.

Further, drying temperature and drying time may affect the solid state properties and/or the solid state form of compounds of the invention (e.g. solvates, hydrates or mixtures thereof). For example, in the case of hydrates, dehydration may occur at low humidities and/or elevated temperatures and/or reduced pressure. For example, following the formation of crystalline monohydrate, there is a critical humidity level below which drying may be performed, which may result in crystal water being lost, and a solid state transformation to an anhydrate occurring. Conversely, anhydrates may be converted (completely or partially) to monohydrates in cases where they are subjected to an atmosphere with a relative humidity that is sufficiently high.

Thus, according to a further aspect of the invention, there is provided a process for the conversion of one crystalline form of a compound of the invention to another, which comprises recrystallising a compound of the invention from an appropriate solvent system, and/or, in the case of interconversion of anhydrate and monohydrate, subjecting the crystalline anhydrate or monohydrate (as appropriate) to an atmosphere with an appropriate relative humidity level.

The preparation, and characterisation, of inter alia anhydrate, monohydrate, and solvate/hydrate forms of compounds of the invention, are described hereinafter. Different crystalline forms of the compounds of the invention (e.g. the anhydrate and the monohydrate) may be readily characterised using X-ray powder diffraction (XRPD) methods, for example as described hereinafter.

Compounds of the invention may be isolated using techniques which are well known to those skilled in the art, for example decanting, filtering or centrifuging.

We have found that, by employing the crystallisation process as described herein, it is possible to produce compounds of the invention with a chemical purity which is above that of the melagatran which is to be isolated in the first instance.

Further purification of compounds of the invention may be effected using techniques which are well known to those skilled in the art. For example impurities may be removed by way of recrystallisation from an appropriate solvent system (e.g. lower alkyl alcohol, such as ethanol or iso-propanol), which may include antisolvent (e.g. iso-octane, acetonitrile, ethyl acetate, methyl ethyl ketone), water, or a combination of these solvents. Suitable temperatures and times for the recrystallisation depend upon the concentration in solution of the compound to be crystallised, and upon the solvent system which is used.

When compounds of the invention are crystallised, or recrystallised, as described herein, the resultant compound is in a form which has the improved chemical and solid state stability mentioned hereinbefore.

Pharmaceutical Preparations and Medical Use p In accordance with the invention, the compounds of the invention may be administered orally, intravenously, subcutaneously, buccally, rectally, dermally, nasally, tracheally, bronchially, by any other parenteral route, or via inhalation, in the form of a pharmaceutical preparation comprising the compound of the invention in a pharmaceutically acceptable dosage form. However, we prefer that the compound of the invention is a form which is suitable for oral or parenteral, such as subcutaneous, administration.

Depending on the disorder, and the patient to be treated, as well as the route of administration, the compounds may be administered at varying doses.

According to a further aspect of the invention, there is provided a pharmaceutical formulation including a compound of the invention in admixture with a pharmaceutically acceptable adjuvant, diluent or carrier. Suitable formulations include those disclosed in international patent applications WO 94/29336, WO 96/14084, WO 96/16671, WO 97/39770, WO 97/45138, WO 98/16252 and WO 00/12043.

The compounds of the invention may be further processed before being admixed with a suitable carrier, diluent or adjuvant. For example, the crystalline form may be milled or ground into smaller particles.

We prefer that formulations comprising compounds of the invention are in a form that is suitable for parenteral (e.g. subcutaneous) delivery. In this respect, compounds of the invention can be admixed with an aqueous solvent carrier system (see, for example, international patent application WO 00/12043) in order to provide a pharmaceutical formulation that is in the form of a liquid and/or a solution.

The amount of compound of the invention which is employed in such a formulation will depend on the condition, and patient, to be treated, as well as the compound (s) which is/are employed, but can be determined non-inventively.

The compounds of the invention are useful because they possess pharmacological activity. They are therefore indicated as pharmaceuticals.

In particular, the compounds of the invention are potent inhibitors of thrombin, for example as demonstrated in the tests described in WO 94/29336. The compounds of the invention are expected to be useful in the treatment of conditions where inhibition of thrombin is required or desirable, including those described in, for example WO 94/29336 and WO 97/23499, the disclosures in which documents are hereby incorporated by reference.

Suitable doses of the compound of the invention in the therapeutic and/or prophylactic treatment of mammalian, especially human, patients are in the range 0.4 to 40 mg per day, and/or 0.0002 to 4 mg/kg (preferably 0.002 to 1 mg/kg) body weight, at parenteral administration, and 2 to 1000 mg-per day, and/or 0.001 to 100 mg/kg (preferably 0.01 to 25 mg/kg) body weight, at oral administration.

According to a further aspect of the invention there is provided a method of treatment of a condition where inhibition of thrombin is required or desired, which method includes administering a therapeutically effective amount of a compound of the invention to a patient in need of such treatment.

For the avoidance of doubt, by "treatment" we include the therapeutic treatment, as well as the prophylaxis, of a condition.

Compounds of the invention have the advantage that they are in a form which provides for improved ease of handling. Further, compounds of the invention have the advantage that they may be produced in forms which have improved chemical and solid state stability. Thus, compounds may be stable when stored over prolonged periods.

Compounds of the invention may also have the advantage that they may be prepared in good yields, in a higher purity, in less time, more conveniently, and at a lower cost, than forms of melagatran prepared previously.

The invention is illustrated, but in no way limited, by the following examples, with reference to the enclosed figures in which.

General Procedures

Figure 1:
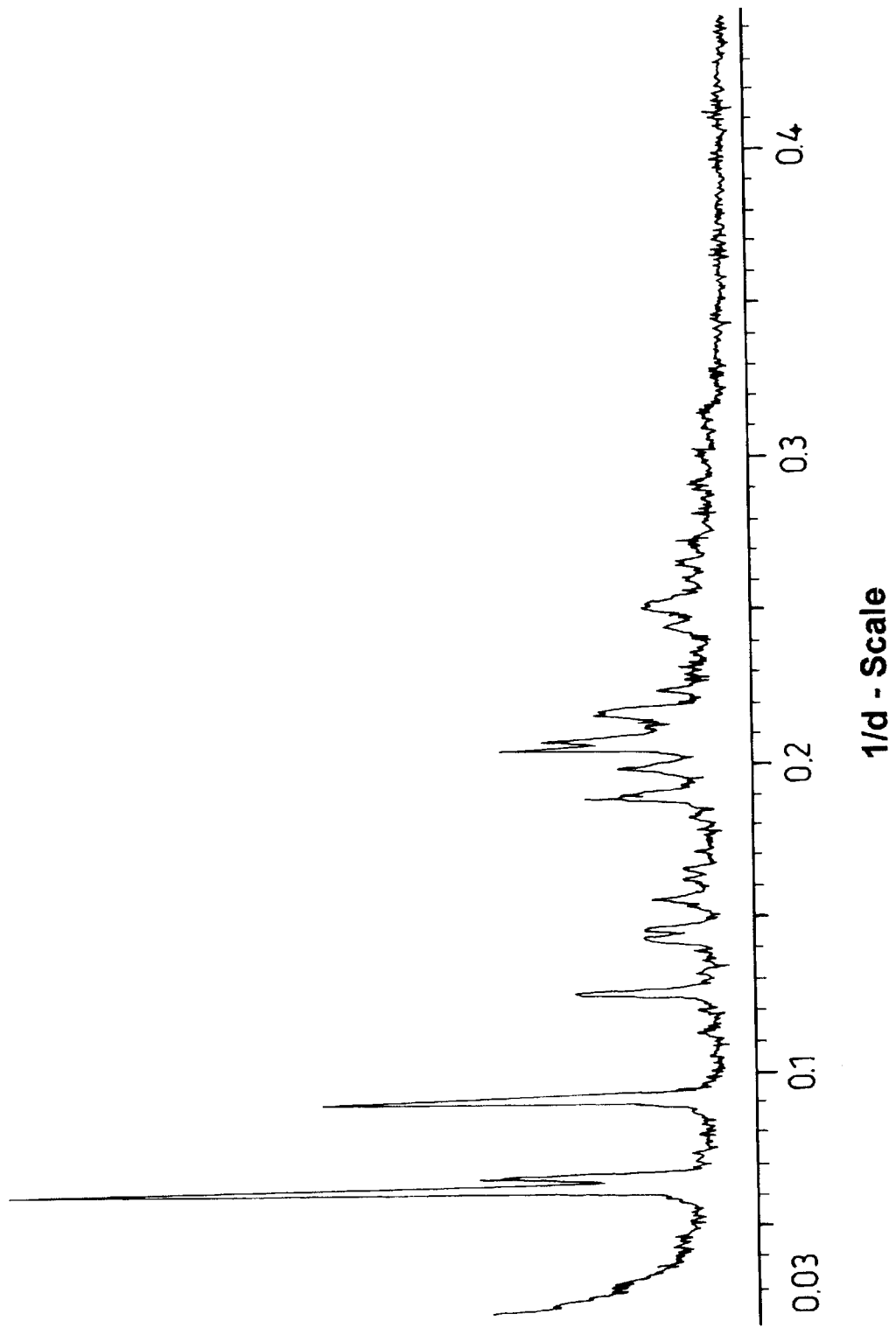
FIG. 1 shows an X-ray powder diffractogram for the crystalline form of melagatran anhydrate obtained by way of Example 2.

X-ray powder diffraction analysis (XRPD) was performed on samples prepared according to standard methods, for example those described in Giacovazzo, C. et al (1995), *Fundamentals of Crystallography*, Oxford University Press; Jenkins, R. and Snyder, R. L. (1996), *Introduction to X-Ray Powder Diffractometry*, John Wiley & Sons, New York; Bunn, C. W. (1948), *Chemical Crystallography*, Clarendon Press, London; or Klug, H. P. & Alexander, L. E. (1974), *X-ray Diffraction Procedures*, John Wiley and Sons, New York. X-ray analyses were performed using a Siemens D5000 diffractometer and/or a Philips X'Pert MPD.

Differential scanning calorimetry (DSC) was performed using a Mettler DSC820 instrument, according to standard methods, for example those described in Hohne, G. W. H. et al (1996), *Differential Scanning Calorimetry*, Springer, Berlin.

Thermogravimetric analysis (TGA) was performed using a Mettler Toledo TGA850 instrument.

Forms prepared in accordance with the Examples below showed "essentially" the same XRPD diffraction patterns and/or DSC thermograms as other Examples disclosed below, when it was clear from the relevant patterns/thermograms (allowing for experimental error) that the same crystalline form had been formed. Thus, limits of experimental error for DSC onset temperatures may be in the range ±5° C. (e.g. ±2° C.), and for XRPD distance values may be in the range ±2 on the last decimal place.

Synthesis of Melagatran Monohydrate

EXAMPLE 1

(a) Boc-(R)Cgl-(S)Aze-Pab-Z DMAP (3.0 eq.) and Boc-(R)Cgl-(S)Aze-OH (1.0 eq.) were dissolved in ethyl acetate:acetonitrile (80:20 v/v) at a volume of 18 L/kg of Boc-(R)Cgl-(S)Aze-OH at 20° C. Pab-Z x HCl (1.15 eq.) was charged into the resultant solution. EDACxHCl (1.4 eq.) was added, and the slurry was stirred at 25° C. for about 3 hours. A sample was removed for in-process process control. The reaction solution was worked up when at least 95% conversion was determined to have taken place. The slurry was then filtered, and the filter cake was washed with ethyl acetate:acetonitrile (80:20 v/v). Aqueous sodium chloride solution (10% w/w) was added and the pH was adjusted to 4.0 with hydrochloric acid solution (4 M). The solution was thoroughly stirred for at least 15 minutes. The water phase was separated off and the organic phase was extracted with aqueous sodium chloride solution (20% w/w). The solution was thoroughly stirred for at least 15 minutes. The water phase was separated off and the organic phase extracted with aqueous sodium chloride solution (10% w/w). The pH was adjusted to 8.0 with aqueous potassium carbonate solution (25% w/w). The solution was thoroughly stirred for at least 15 minutes. The water phase was separated off. Ethyl acetate and acetonitrile were evaporated under vacuum (ca. 15 kPa) at a temperature of ca. 40° C., until the volume in the reactor was approximately 8 L/kg of starting material. More ethyl acetate (13 L/kg of starting material) was added during the evaporation process. A sample was removed for water content analysis. Ethyl alcohol (10% v/v of the total volume) was then added. The solution was used directly in the next step.

(b) H—(R)Cgl-(S)Aze-Pab-Z (i) The solution from step (a) was cooled to 10° C. Methane sulphonic acid (7 eq. per eq. of Boc-(R)Cgl-(S) Aze-Z) was charged, maintaining the temperature below 20° C. The temperature was adjusted to 22° C. and the reaction solution stirred (4 hours) until at least 95% conversion had occurred (as determined by HPLC). The reaction solution was cooled to 10° C. and extracted with a cooled (10° C.) 25% (w/w) aqueous potassium carbonate solution (8 eq. $K_2CO_3$) for at least 15 minutes. The temperature was adjusted to 20° C. and the water phase was separated off. The organic phase was washed with a mixture of aqueous sodium chloride solution (10% w/w) and potassium carbonate (1 eq. $K_2CO_3$) for at least 15 minutes. The water phase was separated off. The solution of the sub-title compound was used directly in the next step.

(ii) The sub-title compound was prepared using essentially the same process as that described in step (b)(i) above, except that the temperature was adjusted to 25° C., and the reaction was stirred for 5 hours, following addition of methane sulphonic acid.

(c) Bzl-OC(O)—CH$_2$—(R)Cgl-(S)Aze-Pab-Z (i) To the reaction solution from step (b)(i) above, further ethyl acetate, water and potassium carbonate (3.0 eq. per eq. of H—(R)Cgl-(S)Aze-Pab-Z) were charged, and the reaction mixture was stirred until the potassium carbonate dissolved. Benzyl bromoacetate (1.2 eq. per eq. of H—(R)Cgl-(S) Aze-Pab-Z) was added and the reactor temperature was increased to 40° C. The temperature was maintained for about 20 hours. A sample was removed for analysis by HPLC. When 95% conversion had occurred, the temperature was decreased to 20° C. and the reaction mixture was allowed to settle for at least 20 minutes. The water phase was separated off and the solution cooled to 10° C. Aqueous sodium chloride solution (4% w/w) was added and the pH adjusted to 4.0 with 4 M hydrochloric acid solution. The two-phase system was thoroughly mixed for at least 15 minutes and allowed to separate for at least 20 minutes. The water phase was separated off. Sodium chloride solution (4% w/w) was added and the pH adjusted to 4.0 with 4 M hydrochloric acid solution. The solution was thoroughly mixed for at least 15 minutes and allowed to separate for at least 20 minutes. The water phase was separated off. Water was added to the resultant solution, which was cooled to 10° C. The pH was adjusted to 2.5 with 4 M hydrochloric acid solution. The two-phase system was thoroughly stirred for at least 15 minutes and allowed to separate for at least 20 minutes. The water phase was separated and charged slowly into a mixture of potassium carbonate in ethyl acetate. The pH was adjusted to 7.0 with 25% (w/w) aqueous potassium carbonate solution and the reaction mixture was thoroughly mixed for at least 15 minutes at 20° C. and allowed to separate for at least 20 minutes. The water phase was separated off. Ethyl acetate was evaporated under vacuum (ca. 10 kPa) at a maximum temperature of 40° C. until the volume in the reaction vessel was about 8.5 L/kg of Boc-(R)Cgl-(S) Aze-OH). More ethyl acetate was added (5 L/kg of Boc-(R)Cgl-(S) Aze-OH) and evaporated again under reduced pressure until the volume in the reaction vessel was about 8.5 L/kg. A sample was taken for water content analysis. If the water content was less than 0.5% (w/v), water was added to give a total water content of 0.5-2.0% (w/v). The temperature was adjusted to 45° C., the reaction solution was seeded with 2% (w/w) of the sub-title compound and the slurry was thoroughly stirred for 10 hours, then cooled to 30° C. over 3 hours and subsequently stirred for at least 3 hours. Toluene (5 L/kg of the sub-title compound) was charged and the slurry was stirred for at least 15 minutes. Ethyl acetate and toluene were evaporated under reduced pressure (ca. 10 kPa) until the volume was the same as before the toluene addition. Toluene (5 L/kg of the sub-title compound) was added and the slurry was stirred for at least 30 minutes. The ethyl acetate and toluene were evaporated again under reduced pressure until the volume was the same as before the toluene addition. Toluene was then added to a total volume of about 11 L/kg of sub-title compound. The slurry was carefully stirred for at least 3 hours at 20° C. The crystals were filtered off and washed with toluene and dried in vacuum (<150 mbar) at approximately 40° C.

(ii) The sub-title compound was prepared using essentially the same process as that described in step (c)(i) above, except that:

(1) before reducing the temperature to 20° C. following addition of benzyl bromoacetate, 96% conversion had occurred; and (2) a third extraction at pH 4 was carried out.

(d) Melagatran Monohydrate (i) Ethanol was charged into a reactor at 20° C. Pd/C (10% w/w of Bzl-OC(O)—CH$_2$—(R)Cgl-(S)Aze-Pab-Z), elutriated in water, was added. (The total amount of water was 6% v/v of total solvent.) Bzl-OC(O)—CH$_2$—(R) Cgl-(S)Aze-Pab-Z (from step (c)(i) above; 8% w/v of total solvent) was charged, and the temperature was raised to 25° C. 3.5 bar pressure of H$_2$ was applied to the reaction mixture, which was stirred vigorously for 5 h. When the reaction was finished (as determined by HPLC), the temperature was set to 20° C., and the reaction slurry was treated with activated carbon (10% w/w of starting material) elutriated in water (0.5 L/kg of starting material) over 0.5 h. The catalyst and carbon were filtered off and the filter cake was washed with ethanol (5 L/kg of melagatran anhydrate). Ethanol was then evaporated at reduced pressure until the volume was 4 L/kg of melagatran anhydrate. iso-Propanol (14 L/kg of melagatran anhydrate) was charged and the solution was again evaporated at reduced pressure (at a temperature between 20 and 30° C.) to a volume of about 7 L/kg of melagatran anhydrate. The solution was filtered and washed with iso-propanol (7 L/kg of melagatran anhydrate). Ethanol/iso-propanol were evaporated at reduced pressure (at a temperature between 20 and 30° C.) to a volume of about 4.4 L/kg of melagatran anhydrate. The water content was analyzed and adjusted to 0.6–0.7 L/kg of melagatran anhydrate. The solution was warmed to 45° C. and acetonitrile (6.0 L/kg of melagatran anhydrate) was added over 20 minutes, whereupon crystallization was started by seeding with the title compound (obtained analogously to the method described in Example 4 below; 2% w/w product). The mixture was stirred for about 15 h. Acetonitrile (6.5 L/kg of melagatran anhydrate) was charged into the vessel. The slurry was stirred at 40° C. for 3 h, then cooled to 20° C. over 1 h and finally stirred at 20° C. for at least 1 h. The crystals were isolated by filtration and washed with acetonitrile:iso-propanol (9:1 (v/v), 3.5 L/kg of the title compound), acetonitrile (2 L/kg of the title compound) and finally ethyl acetate (3 L/kg of the title compound). The crystals were dried at 40° C. and 150-200 mbar.

(ii) The title compound was prepared using essentially the same as that described in process as step (d)(i) above, except that:

(1) the amount of catalyst initially employed was 12% w/w of starting material;

(2) the total amount of water in the reaction was 7% w/v of total solvent;

(3) the filtration following the second evaporation was not carried out;

(4) the in-process control for water content after the evaporations was not carried out (water (0.6 L/kg) was added, instead of adjustments to 0.6 to 0.7 L/kg being carried out);

(5) the amount of washing solvents were:
  (I) acetonitrile:iso-propanol—3 L/kg of melagatran anhydrate;
  (II) acetonitrile—3 L/kg of melagatran anhydrate; and
  (III) ethyl acetate—5 L/kg of melagatran anhydrate;

(6) the drying temperature was 45° C.; and (7) the lower limit for the pressure during drying was 100 mbar.

The crystals were analyzed by XRPD, TGA, GC, DSC and Karl-Fischer titration. They showed essentially the same XRPD pattern, and DSC thermogram, as those exhibited by the form obtained according to Example 4 below.

Crystallisation of Melagatran Anhydrate

EXAMPLE 2

A reaction solution (ethanol:water) containing approximately 64.8 g of melagatran, prepared analogously to the method described in Example 1 above (excluding the last crystallisation step), in a round-bottomed flask, was concentrated by evaporation at reduced pressure until 149 g of solution remained. 200 mL of absolute ethanol was then charged into the vessel, and the solution was concentrated again until 89.5 g remained. A white precipitate was formed. A further 250 mL of absolute ethanol was then charged into the vessel, and the slurry was agitated at 30 to 35° C. until all of the solute was dissolved. The solution was concentrated again until 78.9 g of solution remained. A further 550 mL of absolute ethanol was added, and the suspension was agitated at 38° C. until everything dissolved. The water content was 0.5% (w/w) as determined by Karl-Fischer titration. The solution was filtered, and the filter was washed with 200 mL of absolute ethanol. The solution was heated to 30° C. under a $N_2$-atmosphere, and acetonitrile was charged into the vessel in portions until the solution became opaque (a total of 1380 mL of acetonitrile was charged). The solution was seeded using seed crystals of the title product. The suspension was agitated overnight, and cooled to ambient temperature. The crystals were washed under reduced pressure with 350 mL of a mixture of ethanol and acetonitrile (1:5 (v/v)), and then with acetonitrile (300 mL). The crystals were then dried at 40° C. (0.1 mbar). After 4 hours drying, the particles were milled. The drying was then continued under the same conditions as above for an additional 20 hours.

The crystals were analyzed by XRPD, GC and Karl-Fischer titration. The XRPD result is tabulated below (Table 1) and is shown in FIG. 1.

Karl-Fischer titration showed 1.1% (w/w) water.

TABLE 1

| d value (Å) | intensity (%) | d value (Å) | intensity (%) | d value (Å) | intensity (%) |
|---|---|---|---|---|---|
| 15.9 | 100 | 6.0 | 5 | 4.08 | 10 |
| 15.1 | 30 | 5.8 | 5 | 3.97 | 10 |
| 10.9 | 55 | 5.5 | 5 | 3.82 | 5 |
| 8.9 | 5 | 5.3 | 20 | 3.76 | 5 |
| 8.4 | 5 | 5.0 | 15 | 3.66 | 5 |
| 8.0 | 20 | 4.87 | 30 | 3.44 | 5 |
| 7.0 | 10 | 4.81 | 25 | 3.32 | 5 |
| 6.8 | 10 | 4.71 | 10 | 3.20 | 5 |
| 6.4 | 10 | 4.61 | 15 | | |
| 6.2 | 5 | 4.45 | 5 | | |

EXAMPLE 3

85 mL of a reaction solution (ethanol) containing melagatran, prepared analogously to the process described in Example 1 above (excluding the last crystallisation step) was charged into a 500 mL round-bottomed flask. The solution was concentrated by distillation (pressure: 50 mbar; bath temperature: 70° C.) until 15.3 g of solution remained. 63 mL of iso-propanol was added and the solution was concentrated again as above until 14.8 g remained. A sample was withdrawn, and the water content was 0.93% (v/v) as determined by Karl-Fischer titration. An additional 1.16 mL of purified water was added to the solution in order to improve the filtration. The round-bottomed flask was placed in an oil bath, kept at 40° C. and the solution was agitated using an impeller. 30 mL of acetonitrile was charged slowly into the agitated solution. 80 mg of seed crystals of the title compound were added to the solution, which started to crystallize. The suspension was agitated for an additional 14 hours at 40° C. and then 23 mL of acetonitrile was added. The agitation was continued at 40° C. for 3 hours, the oil bath was then removed, and the suspension was agitated at ambient temperature for 2 hours. The crystals were filtered off under vacuum, washed with a mixture of iso-propanol to and acetonitrile, then with pure acetonitrile, and then dried at 40° C. under reduced pressure. The yield (based on the amount left in the mother liquor) was 84%.

The crystals were analyzed by XRPD, GC and Karl-Fischer titration. They showed essentially the same XRPD pattern as that exhibited by the form obtained according to Example 2 above.

Conversion of Crystalline Melagatran Anhydrate to Crystalline Melagatran Monohydrate

EXAMPLE 4

2 g of melagatran anhydrate (obtained according to the method described in Example 3 above) was charged, together with 1 mL of tap water, 6 mL of iso-propanol and 13.2 mL of acetonitrile, into a 50 mL Erlenmeyer flask. The flask was placed on a shaking table and kept at ambient temperature. The crystals were filtered off after 9 days of agitation/shaking using vacuum and thereafter dried at ambient temperature in a fume hood.

The crystals were analyzed by XRPD, DSC, TGA, GC and Karl-Fischer titration.

Figure 2:
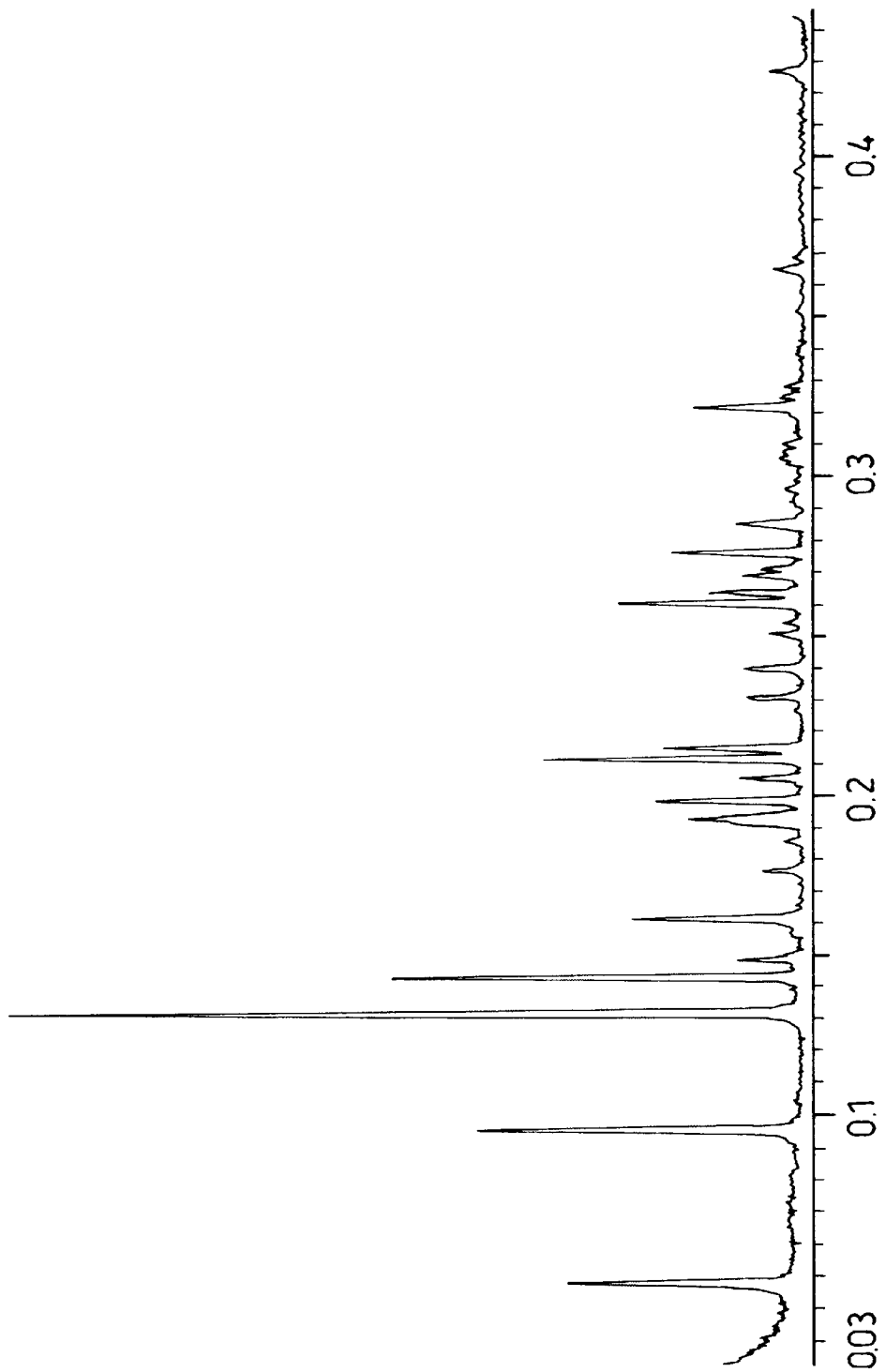
FIG. 2 shows an X-ray powder diffractogram for the crystalline form of melagatran monohydrate obtained by way of Example 4.

The XRPD result is tabulated below (Table 2) and is shown in FIG. 2. DSC showed one endotherm with an onset temperature of ca. 83° C. with an associated heat of −125 J/g (due to dehydration) and one at ca. 210° C. (due to melting).

TGA showed a decrease in mass of ca. 4.3% around 95° C. corresponding to a monohydrate and a decomposition starting around 220° C. Karl-Fisher titration showed 4.3% (w/w) water.

TABLE 2

| d value (Å) | intensity (%) | d value (Å) | intensity (%) | d value (Å) | intensity (%) |
|---|---|---|---|---|---|
| 21.1 | 65 | 5.07 | 55 | 3.63 | 15 |
| 10.5 | 75 | 4.90 | 25 | 3.52 | 20 |
| 7.6 | 90 | 4.75 | 60 | 3.39 | 5 |
| 7.0 | 100 | 4.68 | 50 | 3.27 | 10 |
| 6.7 | 10 | 4.35 | 15 | 3.23 | 5 |
| 6.4 | 5 | 4.19 | 20 | 3.12 | 20 |
| 6.2 | 25 | 4.00 | 10 | 3.09 | 10 |
| 5.7 | 5 | 3.94 | 5 | 3.06 | 5 |
| 5.4 | 10 | 3.85 | 20 | 2.75 | 5 |
| 5.3 | 30 | 3.81 | 15 | 2.38 | 10 |
| 5.22 | 45 | 3.73 | 10 | 2.35 | 10 |
| 5.19 | 25 | 3.70 | 10 | | |

EXAMPLE 5

139 kg of ethyl acetate was charged into a reactor together with 10.3 kg of melagatran anhydrate (from Example 9 below), followed by 1.9 kg of purified water (4.5 equivalents). The suspension was agitated for 16–20 hours at 40° C. Following cooling to 25° C., the suspension was agitated for an additional 2 days. The slurry was then filtered using pressure filtration, and the reactor and filter cake were washed with 46 kg of ethyl acetate. The crystals were dried at reduced pressure (150±50 mbar) and 40° C. for several days.

The crystals were analyzed by XRPD, DSC, TGA, GC and Karl-Fischer titration. They showed essentially the same XRPD pattern, and DSC thermogram, as those exhibited by the form obtained according to Example 4 above. Karl-Fischer titration showed a water content of 4.0% (w/w).

Conversion of one Crystalline Form of Melagatran Anhydrate to another Crystalline Form of Melagatran Anhydrate

EXAMPLE 6

2.5 g of melagatran anhydrate (from Example 2 above) was charged, together with 6 mL of iso-propanol, 1.0 mL of tap water and 13.2 mL of acetonitrile, into a 50 mL Erlenmeyer flask. The flask was placed on a shaking table, where it was left for 9 days. The crystals were filtered under vacuum and then dried at 40° C. and at a pressure of less than 20 mbar overnight.

The crystals were analyzed by XRPD, DSC, GC and Karl-Fischer titration.

Figure 3:
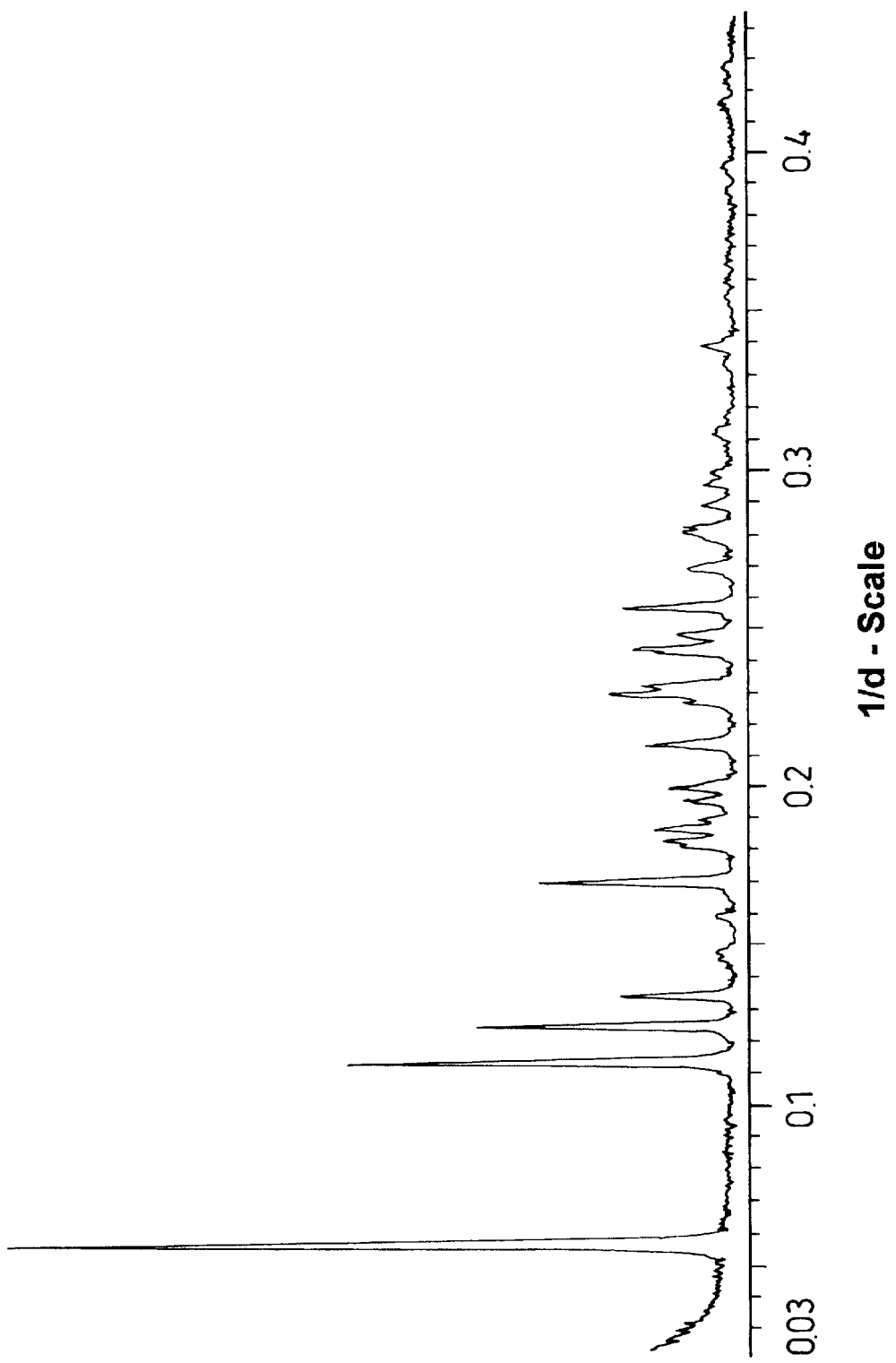
FIG. 3 shows an X-ray powder diffractogram for the crystalline form of melagatran anhydrate obtained by way of Example 6.

The XRPD result is tabulated below (Table 3) and is shown in FIG. 3.

DSC showed an endotherm with an extrapolated onset temperature of 210° C. associated with a heat of −120 J/g.

TABLE 3

| d value (Å) | intensity (%) | d value (Å) | intensity (%) | d value (Å) | intensity (%) |
|---|---|---|---|---|---|
| 17.8 | 100 | 4.43 | 5 | 3.28 | 1 |
| 8.9 | 45 | 4.38 | 15 | 3.24 | 1 |
| 8.1 | 20 | 4.33 | 10 | 3.17 | 1 |
| 7.5 | 10 | 4.14 | 5 | 3.09 | 1 |
| 6.9 | 5 | 4.12 | 10 | 3.01 | 1 |
| 6.3 | 5 | 4.05 | 10 | 2.96 | 5 |
| 5.9 | 25 | 3.91 | 10 | 2.83 | 1 |
| 5.6 | 10 | 3.73 | 10 | 2.54 | 1 |
| 5.5 | 10 | 3.61 | 5 | 2.49 | 1 |
| 5.4 | 10 | 3.58 | 5 | 2.41 | 1 |
| 5.3 | 5 | 3.56 | 5 | 2.38 | 5 |
| 5.2 | 5 | 3.47 | 5 | 2.35 | 1 |
| 5.0 | 10 | 3.40 | 5 | | |
| 4.71 | 10 | 3.36 | 5 | | |

EXAMPLE 7

3.0 g of melagatran anhydrate (from Example 2 above) was charged, together with 0.5 mL of tap water and 20 mL of ethyl acetate, into a 50 mL Erlenmeyer flask. The flask was placed on a shaking table, where it was left for 9 days. The crystals were filtered under vacuum, washed with ethyl acetate and then dried at 40° C. and at a pressure of less than 20 mbar overnight.

The crystals were analyzed by XRPD, DSC, GC and Karl-Fischer titration. They showed essentially the same XRPD pattern, and DSC thermogram, as those exhibited by the form obtained according to Example 6 above.

EXAMPLE 8

3.0 g of melagatran anhydrate (from Example 2 above) was charged, together with 0.5 mL of tap water and 20 mL of methyl iso-butyl ketone, into a 50 mL Erlenmeyer flask. The flask was placed on a shaking table, where it was left for 9 days. The crystals were filtered under vacuum, washed with methyl iso-butyl ketone, and then dried at 40° C. and at a pressure of less than 20 mbar overnight.

The crystals were analyzed by XRPD, DSC, GC and Karl-Fischer titration. They showed essentially the same XRPD pattern, and DSC thermogram, as those exhibited by the form obtained according to Example 6 above.

Conversion of Crystalline Melagatran Monohydrate to Crystalline Melagatran Anhydrate

EXAMPLE 9

Crystals of monohydrate (from Example 1 above) were dried at reduced pressure (<15–20 mbar) and 40° C. until the water content was less than 1.0% (w/w).

The crystals were analyzed by XRPD, DSC, GC and Karl-Fischer titration. They showed essentially the same XRPD pattern, and DSC thermogram, as those exhibited by the form obtained according to Example 6 above.

Crystallisation of Melagatran iso-Propanolate/Hydrate

EXAMPLE 10

2.0 g of melagatran anhydrate (from Example 3 above) was added to an Erlenmeyer flask. 5.5 mL of iso-propanol, 2.5 mL of ethanol, 1.4 mL of purified water and 24 mL of acetonitrile were then charged into the flask. A magnetic bar was placed in the flask, which was placed on a shaking table, kept at ambient temperature. The suspension was agitated for 7 days. The crystals were filtered under vacuum and then dried at 40° C., at a pressure of less than 20 mbar overnight.

Figure 4:
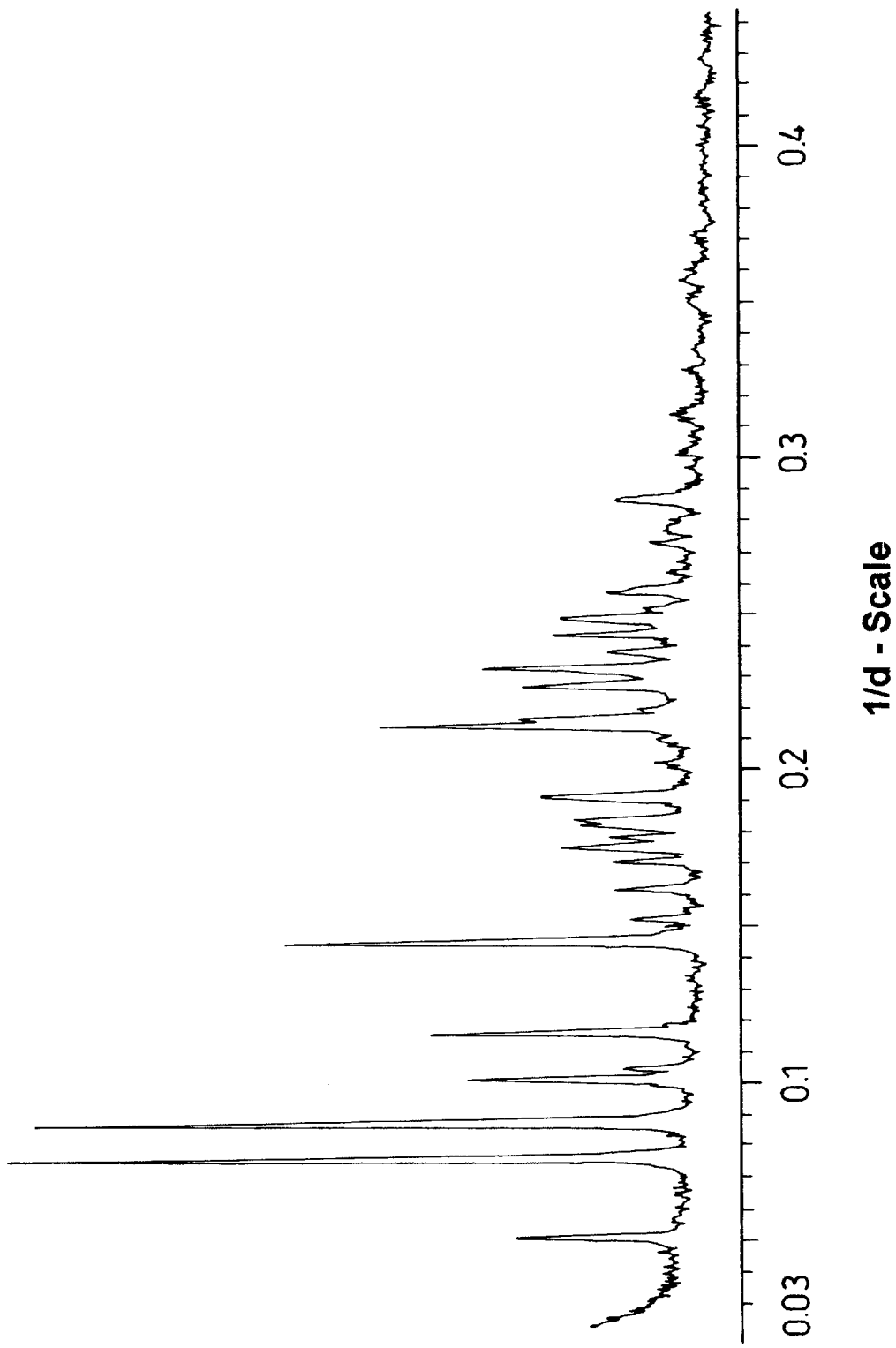
FIG. 4 shows an X-ray powder diffractogram for the crystalline form of melagatran iso-propanolate/hydrate obtained by way of Example 10.

The crystals were analyzed by XRPD, DSC, TGA, GC and Karl-Fischer titration. The XRPD result is tabulated below (Table 4) and is shown in FIG. 4.

GC showed 4.0% (w/w) iso-propanol and Karl-Fischer titration showed 6.5% (w/w) water. The results indicated that a mixed iso-propanolate/hydrate had been formed.

TGA showed a decrease in mass of ca. 4.6% around 55° C., and a decrease in mass of ca. 5.6% around 140° C.

TABLE 4

| d value (Å) | intensity (%) | d value (Å) | intensity (%) | d value (Å) | intensity (%) |
|---|---|---|---|---|---|
| 19.7 | 25 | 5.4 | 15 | 3.67 | 10 |
| 13.1 | 100 | 5.2 | 25 | 3.61 | 5 |
| 11.4 | 95 | 4.95 | 5 | 3.49 | 15 |
| 9.9 | 35 | 4.77 | 5 | 3.31 | 5 |
| 9.6 | 10 | 4.66 | 45 | 3.18 | 5 |
| 8.6 | 40 | 4.62 | 25 | 3.05 | 5 |
| 6.9 | 60 | 4.55 | 10 | 2.99 | 5 |
| 6.6 | 10 | 4.40 | 25 | 2.85 | 5 |
| 6.2 | 15 | 4.29 | 35 | 2.80 | 5 |
| 5.9 | 15 | 4.20 | 15 | 2.69 | 5 |
| 5.7 | 20 | 4.11 | 25 | 2.62 | 1 |
| 5.6 | 15 | 4.02 | 20 | 2.40 | 5 |
| 5.5 | 15 | 3.88 | 15 | 2.33 | 5 |

Abbreviations
(S)aze=(S)-azetidine-2-carboxylate
Boc=tert-butyloxycarbonyl
Bzl=benzyl
(R)Cgl=(R)-cyclohexylglycine
DMAP=4-dimethylaminopyridine
EDAC=1-ethyl-3-(3-dimethylaminopropyl)-carbodiimide
Pab-H=4-aminomethylamidinobenzene
Z=benzyloxycarbonyl

What is claimed is:

1. A substantially crystalline form of melagatran which is in the form of a hydrate.

2. A substantially crystalline form of melagatran which contains at least 0.5 mol of water per mol of melagatran.

3. A compound as claimed in claim 1, characterised by a differential scanning calorimetry curve, at a heating rate of 10° C./min in a closed cup with a pinhole under flowing nitrogen, exhibiting an endotherm with an extrapolated onset temperature of about 83° C. and an associated heat of about −125 J/gram; an X-ray powder diffraction pattern characterised by crystalline peaks with d-values at 21.1, 10.5, 7.6, 7.0, 6.7, 6.4, 6.2, 5.7, 5.4, 5.3, 5.22, 5.19, 5.07, 4.90, 4.75, 4.68, 4.35, 4.19, 4.00, 3.94, 3.85, 3.81, 3.73, 3.70, 3.63, 3.52, 3.39, 3.27, 3.23, 3.12, 3.09, 3.06, 2.75, 2.38 and 2.35 Å; and/or a water content of 4.3% (w/w).

4. A substantially crystalline form of melagatran which is in the form of an anhydrate.

5. A compound as claimed in claim 4 characterised by an X-ray powder diffraction pattern characterised by crystalline peaks with d-values at 15.9, 15.1, 10.9, 8.9, 8.4, 8.0, 7.0, 6.8, 6.4, 6.2, 6.0, 5.8, 5.5, 5.3, 5.0, 4.87, 4.81, 4.71, 4.61, 4.45, 4.08, 3.97, 3.82, 3.76, 3.66, 3.44, 3.32 and 3.20 Å.

6. A compound as claimed in claim 4, characterised by a differential scanning calorimetry curve, at a heating rate of 10° C./min in a closed cup with a pinhole under flowing nitrogen, exhibiting an endotherm with an extrapolated onset temperature of about 210° C. and an associated heat of about −120 J/g; and/or an X-ray powder diffraction pattern characterised by crystalline peaks with d-values at 17.8, 8.9, 8.1, 7.5, 6.9, 6.3, 5.9, 5.6, 5.5, 5.4, 5.3, 5.2, 5.0, 4.71, 4.43, 4.38, 4.33, 4.14, 4.12, 4.05, 3.91, 3.73, 3.61, 3.58, 3.56, 3.47, 3.40, 3.36, 3.28, 3.24, 3.17, 3.09, 3.01, 2.96, 2.83, 2.54, 2.49, 2.41, 2.38 and 2.35 Å.

7. A substantially crystalline form of melagatran which is in the form of a mixed iso-propanolate/hydrate.

8. A compound as claimed in claim 7, characterised by an X-ray powder diffraction pattern characterised by crystalline peaks with d-values at 19.7, 13.1, 11.4, 9.9, 9.6, 8.6, 6.9, 6.6, 6.2, 5.9, 5.7, 5.6, 5.5, 5.4, 5.2, 4.95, 4.77, 4.66, 4.62, 4.55, 4.40, 4.29, 4.20, 4.11, 4.02, 3.88, 3.67, 3.61, 3.49, 3.31, 3.18, 3.05, 2.99, 2.85, 2.80, 2.69, 2.62, 2.40 and 2.33 Å.

9. A process for the production of a compound as claimed in any one of claims 1 to 8, which comprises crystallising melagatran.

10. A process as claimed in claim 9, which comprises crystallising melagatran from a solvent.

11. A process as claimed in claim 10, wherein the solvent is selected from the group: lower alkyl acetates, lower alkyl alcohols, aliphatic and aromatic hydrocarbons, dialkyl ethers, dialkyl ketones, acetonitrile, aqueous solutions, or mixtures thereof.

12. A process as claimed in claim 11 wherein the solvent is selected from the group: $C_{1-6}$ alkyl acetates, $C_{1-6}$ alkyl alcohols, $C_{5-12}$ aliphatic hydrocarbons, $C_{6-10}$ aromatic hydrocarbons, di-$C_{1-6}$ alkyl ethers, di-$C_{1-6}$ alkyl ketones, acetonitrile, water, or mixtures thereof.

13. A process as claimed in claim 12 wherein the solvent is selected is from the group: ethyl acetate, ethanol, iso-propanol, iso-octane, n-heptane, toluene, di-iso-propyl ether, methyl iso-butyl ketone, acetonitrile, water, or mixtures thereof.

14. A process as claimed in any one of claim 9, in which at least one lower alkyl alcohol and/or water is used as solvent and acetonitrile and/or ethyl acetate is/are used as antisolvent.

15. A process for the production of a substantially crystalline form of melagatran which is in the form of an anhydrate which comprises a process according to claim 14, in which the solvent is substantially free of water.

16. A process for the production of a substantially crystalline form of melagatran which is in the form of a hydrate, which comprises a process according to claim 10, in which the solvent contains water.

17. A process for the conversion of one crystalline form of a compound as claimed in claim 1 or claim 14 to another which comprises recrystallising that first-mentioned crystalline form from an appropriate solvent system.

18. A process for the interconversion of an anhydrate compound as claimed in claim 4, and a hydrate compound claim 1, which comprises subjecting the crystalline anhydrate or hydrate to an atmosphere with an appropriate relative humidity level.

19. A compound obtainable by a process according to claim 9.

20. A pharmaceutical formulation including a compound as claimed in any one of claims 1 to 8 in admixture with a pharmaceutically acceptable adjuvant, diluent or carrier.

21. A formulation as claimed in claim 20, which comprises an aqueous solution of the compound.

22. A method of treatment of a condition where inhibition of thrombin is required or desired which method comprises administering a therapeutically effective amount of a compound according to any one of claims 1 to 8 to a patient in need of such treatment.

23. A process for the production of a substantially crystalline form of melagatran which contains at least 0.5 mol of water per mol of melagatran, which comprises a process according to claim 10, in which the solvent contains water.

24. A process for the production of a substantially crystalline form of melagatran, characterised by a differential scanning calorimetry curve, at a heating rate of 10° C./min in a closed cup with a pinhole under flowing nitrogen, exhibiting an endotherm with an extrapolated onset temperature of about 83° C. and an associated heat of about −125 J/gram; an X-ray powder diffraction pattern characterised by crystalline peaks with devalues at 21.1, 10.5, 7.6, 7.0, 6.7, 6.4, 6.2, 5.7, 5.4, 5.3, 5.22, 5.19, 5.07, 4.90, 4,75, 4,68, 4,35, 4,19, 4.00, 3.94, 3.85, 3.81, 3.73, 3.70, 3.63, 3.52, 3.39, 3.27, 3.23, 3.12, 3.09, 3.06, 2.75, 2.38 and 2.35 Å; and/or a water content of 4.3% (w/w), which comprises a process according to claim 10 in which the solvent contains water.

* * * * *

UNITED STATES PATENT AND TRADEMARK OFFICE
CERTIFICATE OF CORRECTION

PATENT NO. : 6,479,078 B1 Page 1 of 1
DATED : November 12, 2002
INVENTOR(S) : Hedstrom et al.

It is certified that error appears in the above-identified patent and that said Letters Patent is hereby corrected as shown below:

Column 16,
Line 7, please delete "14" and insert -- 10 --.
Line 14, please delete "as claimed in claim 1 or claim 14" and insert -- as claimed in claim 1 or claim 4 --.
Line 47, please delete "4,75," and insert -- 4.75, --.
Line 48, please delete "4,68, 4,35, 4,19" and insert -- 4.68, 4.35, 4.19 --.

Signed and Sealed this

Twenty-third Day of December, 2003

JAMES E. ROGAN
*Director of the United States Patent and Trademark Office*